(12) United States Patent
Goldman et al.

(10) Patent No.: US 11,739,137 B2
(45) Date of Patent: Aug. 29, 2023

(54) SINGLE DOMAIN ANTIBODIES TO SARS-COV-2 NUCLEOCAPSID PROTEIN

(71) Applicant: The Government of the United States of America, as represented by the Secretary of the Navy, Arlington, VA (US)

(72) Inventors: Ellen R. Goldman, Germantown, MD (US); George P. Anderson, Bowie, MD (US); Jinny L. Liu, Ellicot City, DC (US); Thomas J. Esparza, Frederick, MD (US)

(73) Assignee: The Government of the United States of America, as represented by the Secretary of the Navy, Arlington, VA (US)

( * ) Notice: Subject to any disclaimer, the term of this patent is extended or adjusted under 35 U.S.C. 154(b) by 0 days.

(21) Appl. No.: 17/512,837

(22) Filed: Oct. 28, 2021

(65) Prior Publication Data
US 2022/0135654 A1  May 5, 2022

Related U.S. Application Data

(60) Provisional application No. 63/107,595, filed on Oct. 30, 2020.

(51) Int. Cl.
*C07K 16/10* (2006.01)
*C07K 16/46* (2006.01)
*G01N 33/563* (2006.01)
*G01N 33/569* (2006.01)
*A61K 39/00* (2006.01)

(52) U.S. Cl.
CPC ............ *C07K 16/10* (2013.01); *C07K 16/468* (2013.01); *G01N 33/563* (2013.01); *G01N 33/56983* (2013.01); *A61K 2039/507* (2013.01); *C07K 2317/21* (2013.01); *C07K 2317/31* (2013.01); *C07K 2317/565* (2013.01); *C07K 2317/569* (2013.01); *C07K 2317/92* (2013.01); *G01N 2333/165* (2013.01)

(58) Field of Classification Search
CPC .......... C07K 2317/22; C07K 2317/569; C07K 16/10
USPC .............................................. 424/133.1, 136.1
See application file for complete search history.

(56) References Cited

U.S. PATENT DOCUMENTS

| | | | | |
|---|---|---|---|---|
| 9,334,331 | B2 * | 5/2016 | Igawa ................... | C07K 16/40 |
| 10,421,807 | B2 * | 9/2019 | Gonzales ............... | A61P 11/00 |
| 11,149,094 | B2 * | 10/2021 | Chiu .................. | C07K 16/241 |
| 2005/0226863 | A1 | 10/2005 | Colby et al. | |

OTHER PUBLICATIONS

Al Qaraghuli et al. (2020, Nature Scientific Reports 10:13969).*
Edwards et al. (2003, JMB 334:103-118).*
Lloyd et al. (2009, Protein Engineering, Eng. Design & Selection 22(3): 159-168).*
Goel et al. (2004, J. Immunol. 173: 7358-7367).*
Khan et al. (2014, J. Immunol. 192: 5398-5405).*
Poosarla et al. (2017, Biotechn. Bioeng. 114(6): 1331-1342).*
Konwarh (Front Immunol Jun. 23, 2020;11:1531. doi: 10.3389/fimmu.2020.01531. eCollection 2020.*
Gransagne et al (The Journal of biological chemistry, (Jan. 2022) vol. 298, No. 1, pp. 101290. Electronic Publication Date: Oct. 20, 2021).*
Zarebski LM, Urrutia M, Goldbaum FA. Llama single domain antibodies as a tool for molecular mimicry. J Mol Biol. Jun. 17, 2005;349(4):814-24. doi: 10.1016/j.jmb.2005.03.072. Epub Apr. 21, 2005. PMID: 15890359.
Characterization and application of monoclonal antibodies against N protein of SARS-coronavirus Bo Shang, Xiao-Yi Wang, Jian-Wei Yuan, Astrid Vabret, Xiao-Dong Wu, Rui-Fu Yang, Lin Tian, Yong-Yong Ji, Vincent Deubel, Bing Sun Biochem Biophys Res Commun. Oct. 14, 2005; 336(1): 110-117. Published online Aug. 15, 2005. doi 10.1016/j.bbrc.2005.08.032 PMCID: PMC7092910.

* cited by examiner

*Primary Examiner* — Lynn A Bristol
(74) *Attorney, Agent, or Firm* — US Naval Research Laboratory; Roy Roberts

(57) ABSTRACT

A number of single domain antibodies (sdAb, also known as nanobodies or VHH) were developed that bind nucleocapsid protein of the SARS-CoV-2 virus. They are useful for detecting the virus and could also find application in therapeutics.

4 Claims, 9 Drawing Sheets

Specification includes a Sequence Listing.

SINGLE DOMAIN ANTIBODIES TO SARS-COV-2 NUCLEOCAPSID PROTEIN

CROSS-REFERENCE TO RELATED APPLICATIONS

This application claims the benefit of U.S. Provisional Patent Application No. 63/107,595 filed Oct. 30, 2020, the entirety of which is incorporated herein by reference.

FEDERALLY-SPONSORED RESEARCH AND DEVELOPMENT

The United States Government has ownership rights in this invention. Licensing inquiries may be directed to Office of Technology Transfer, US Naval Research Laboratory, Code 1004, Washington, DC 20375, USA; +1.202.767.7230; techtran@nrl.navy.mil, referencing NC 113715.

BACKGROUND

The severe acute respiratory syndrome coronavirus of 2019 (SARS-CoV-2) is known to cause the coronavirus disease of 2019 (COVID-19). According to the World Health Organization, as of Oct. 28, 2021, the global SARS-CoV-2 viral pandemic has resulted in over 244 million COVID-19 cases around the world and nearly five million deaths.

The SARS-CoV-2 genome is composed of approximately 30,000 nucleotides, which encodes four structural proteins: spike (S) protein, envelope (E) protein, membrane (M) protein, and nucleocapsid (N) protein [1]. N protein is a highly immunogenic and an abundantly expressed protein during infection [2,3].

After infection, the N protein enters the host cell together with the viral RNA to facilitate replication and process assembly and release of the virus particle [4]. SARS-CoV N protein contains two distinct RNA-binding domains (the N-terminal domain [NTD] and the C-terminal domain [CTD]) linked by a poorly structured linkage region (LKR) containing a serine/arginine-rich (SR-rich) domain (SRD) [5,6]. Due to the positive amino acids, SARS-CoV N-NTD and N-CTD have been reported to bind with viral RNA genome [7,8]. LKR appears to improve oligomerization [9,10]. However, as of this writing, the molecular properties of SARS-CoV-2 N protein remain to be elucidated.

SARS-CoV-2 N protein is a dimer in solution by CTD-CTD interaction [11]. Additionally, N protein can bind with non-specific dsDNA probably by its electrostatic interaction.

For SARS-CoV-2 infection, early diagnosis is particularly important not only to facilitate proper patient care, but to ensure the safety of the community [12]. Detection methods have been rapidly improving due to the deepening understanding of COVID-19. Nucleic acid testing, chest CT, confirmation of epidemiological history and clinical manifestations are important bases for the diagnosis of COVID-19 [12-15]. However, nucleic acid testing requires skilled technicians, is time-consuming, and costly. In comparison, the coronavirus antigen detection method has the advantages of being rapid, relatively easy to perform, and the SARS-CoV antigen can be detected up to 1 day before appearance of clinical symptoms [16].

Theoretically, viral antigen is the specific marker of the virus and precedes antibody appearance within infected people. Therefore, detection of viral antigen can fill the role for a rapid screening assay, achieving the critical early diagnosis required to limit further viral spread. While to date, assays for SARS-CoV-2 nucleocapsid protein have relied upon conventional antibodies, in the future this role may be subsumed by high affinity single domain antibodies tailored for the detection platform to enhance the sensitivity and consistency of the detection methodology.

Single domain antibodies (sdAb, also known as nanobodies or VHH) are the variable domains derived from the unconventional heavy chain only antibodies found in camelids, and combine the specificity and affinity of conventional antibodies with the ability to be easily produced recombinantly and engineered towards specific applications. Other advantages of sdAb include their small size, about one tenth the size of conventional antibodies (~15 kDa versus ~150 kDa), their ability to refold and bind antigen after denaturation, and the ability to recognize hidden epitopes not recognized by conventional antibodies. The ability to engineer sdAb and to readily produce them as genetic fusions, along with their innate stability make them ideal recognition elements for incorporation into diagnostic assays.

SdAb also exhibit properties that are advantageous for therapeutics including their good tissue penetration in vivo, low immunogenicity, and ability to tune the serum half-life through PEGylation or genetic fusions. Additionally, sdAb have a proven safety profile. For example, Ablynx, a Sanofi company based in Belgium currently has multiple sdAb in clinical development and the first product (caplacizumab for the treatment of acquired thrombotic thrombocytopenic purpura, TTP) was approved by the United States Food and Drug Administration in early February 2019.

A need exists for new techniques for the detection and treatment of SARS-CoV-2.

BRIEF SUMMARY

In one embodiment, an isolated variable domain of a camelid heavy-chain antibody (VHH), also known as a single domain antibody (sdAb) or nanobody, directed against the nucleocapsid protein (N) of SARS-CoV-2 has an amino acid sequence selected from the group consisting of SEQ ID NOs: 1 through 16.

In another embodiment, a sdAb capable of binding to SARS-CoV-2 N, has an overall amino acid sequence identity of at least 70% to a sequence selected from the group consisting of SEQ ID NOs: 1 through 16, while having an amino acid sequence identity in CDR1, CDR2, and CDR3 regions of at least 75%.

A further embodiment is an isolated sdAb comprising complementarity determining regions (CDRs) identified as CDR1, CDR2, and CDR3 and having a protein sequence with at least 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100% with respect to corresponding CDR regions in a sequence selected from the group consisting of SEQ ID NOs: 1 through 16. In a further aspect, the isolated sdAb has an amino acid sequence identity in the CDR1, CDR2, and CDR3 regions are greater than 75%, for example 76, 77, 78, 79, 80, 81, 82, 83, 84, 85, 86, 87, 88, 89, 90, 91, 92, 93, 94, 95, 96, 97, 98, 99 or 100%, to corresponding CDR regions in the sequence selected from the group consisting of SEQ ID NOs: 1 through 16.

In a still further embodiment, an isolated bivalent antibody comprises any two sbAb antibodies as described above joined to one another with a polypeptide linker therebetween, wherein the antibodies are the same (homobivalent) or different (heterobivalent). In an even further embodiment, an isolated multivalent antibody comprises at least two sdAb antibodies joined together as described above.

In yet another embodiment, a polypeptide comprising an antibody as described above incorporates an additional amino sequence configured to provide a desired function.

In an additional embodiment, a method of detecting SARS-CoV-2 contacting a sample known or suspected of comprising SARS-CoV-2 with an antibody as described above and detecting presence of nucleocapsid protein from SARS-CoV-2 in the sample by receiving a signal indicating binding to the antibody, where a signal greater than a limit of detecting indicates the presence of SARS-CoV-2 in the sample.

In a still further embodiment, a method of treating SARS-CoV-2 infection includes contacting a sample from a patient known to or suspected of being infected with SARS-CoV-2 with an antibody according to any of the above embodiments; detecting presence of nucleocapsid protein from SARS-CoV-2 in the sample by receiving a signal indicating binding to the antibody; and if, the nucleocapsid protein is detected, then treating the patient for SARS-CoV-2 infection.

In one more embodiment, a nucleotide sequence encodes an antibody as described above.

BRIEF DESCRIPTION OF THE DRAWINGS

FIGS. 1A and 1B show sequence alignments of sdAb directed against SARS-CoV-2 nucleocapsid protein. FIG. 1A is a sequence alignment of the 16 clones identified by the monoclonal phage MagPlex® assay. Sequences are given in the single letter amino acid code; bold-format letters denotes high homology position, while lower homology positions are in italics. Positions are numbered sequentially. Using this numbering scheme, we define CDR1 as the region of amino acid residues 26-35, CDR2 as residues 50-65, and CDR3 as residues 99-119. The clones B6, E2, C2, E10, and A8 (shown together in FIG. 1B) were expressed as soluble sdAbs FIG. 2 provides results of a direct-binding MagPlex® assay to determine the ability of purified representatives from each of the five sequence families binding to the bead-immobilized N. Two sets of N-coated microspheres were averaged with the error bars (standard error of the mean) shown, along with a set of SARS-CoV-2 receptor-binding domain (RBD)-coated microspheres which had little-to-no signal and are not shown.

DETAILED DESCRIPTION

Definitions

Figure 2:
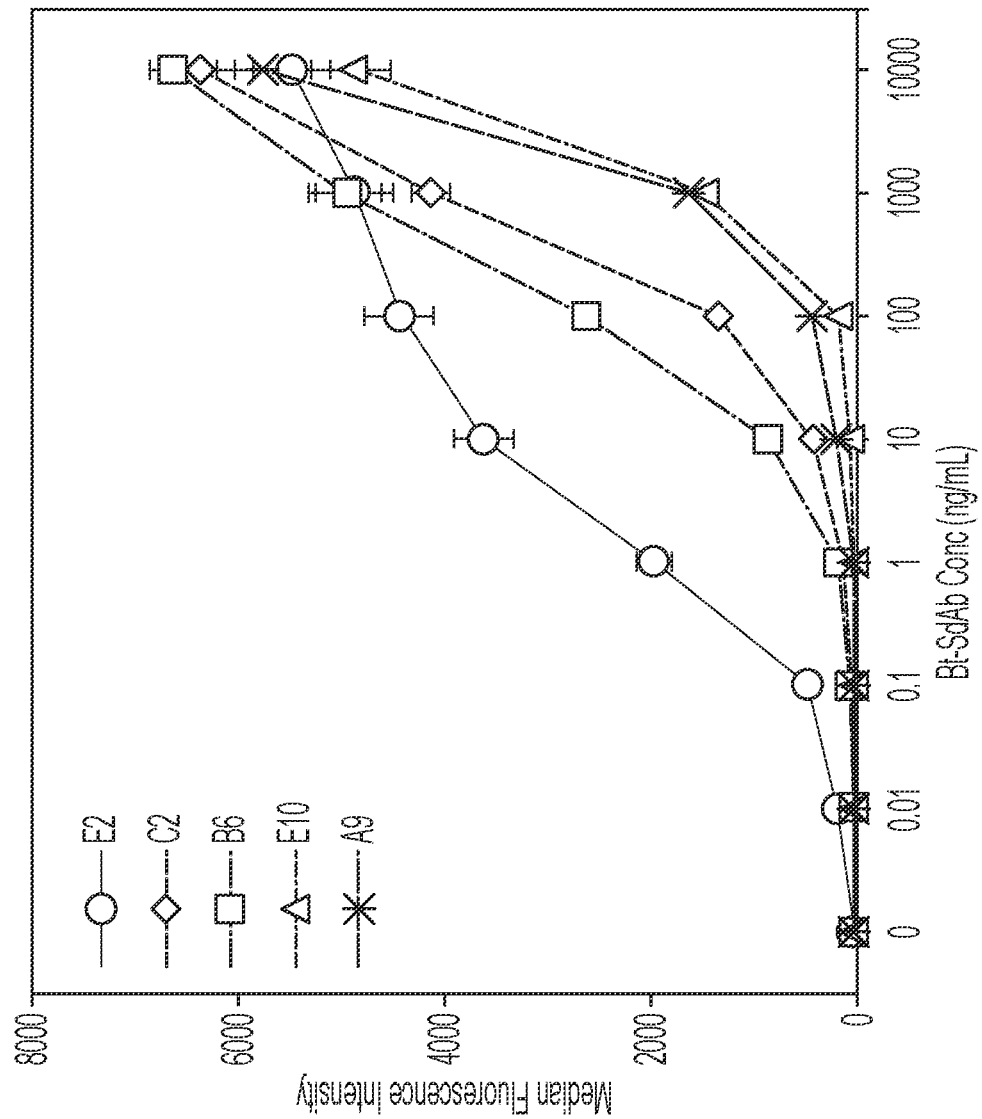

Before describing the present invention in detail, it is to be understood that the terminology used in the specification is for the purpose of describing particular embodiments, and is not necessarily intended to be limiting. Although many methods, structures and materials similar, modified, or equivalent to those described herein can be used in the practice of the present invention without undue experimentation, the preferred methods, structures and materials are described herein. In describing and claiming the present invention, the following terminology will be used in accordance with the definitions set out below.

As used herein, the singular forms "a", "an," and "the" do not preclude plural referents, unless the content clearly dictates otherwise.

As used herein, the term "and/or" includes any and all combinations of one or more of the associated listed items.

As used herein, the term "about" when used in conjunction with a stated numerical value or range denotes somewhat more or somewhat less than the stated value or range, to within a range of ±10% of that stated.

Figures 1A, 1B:
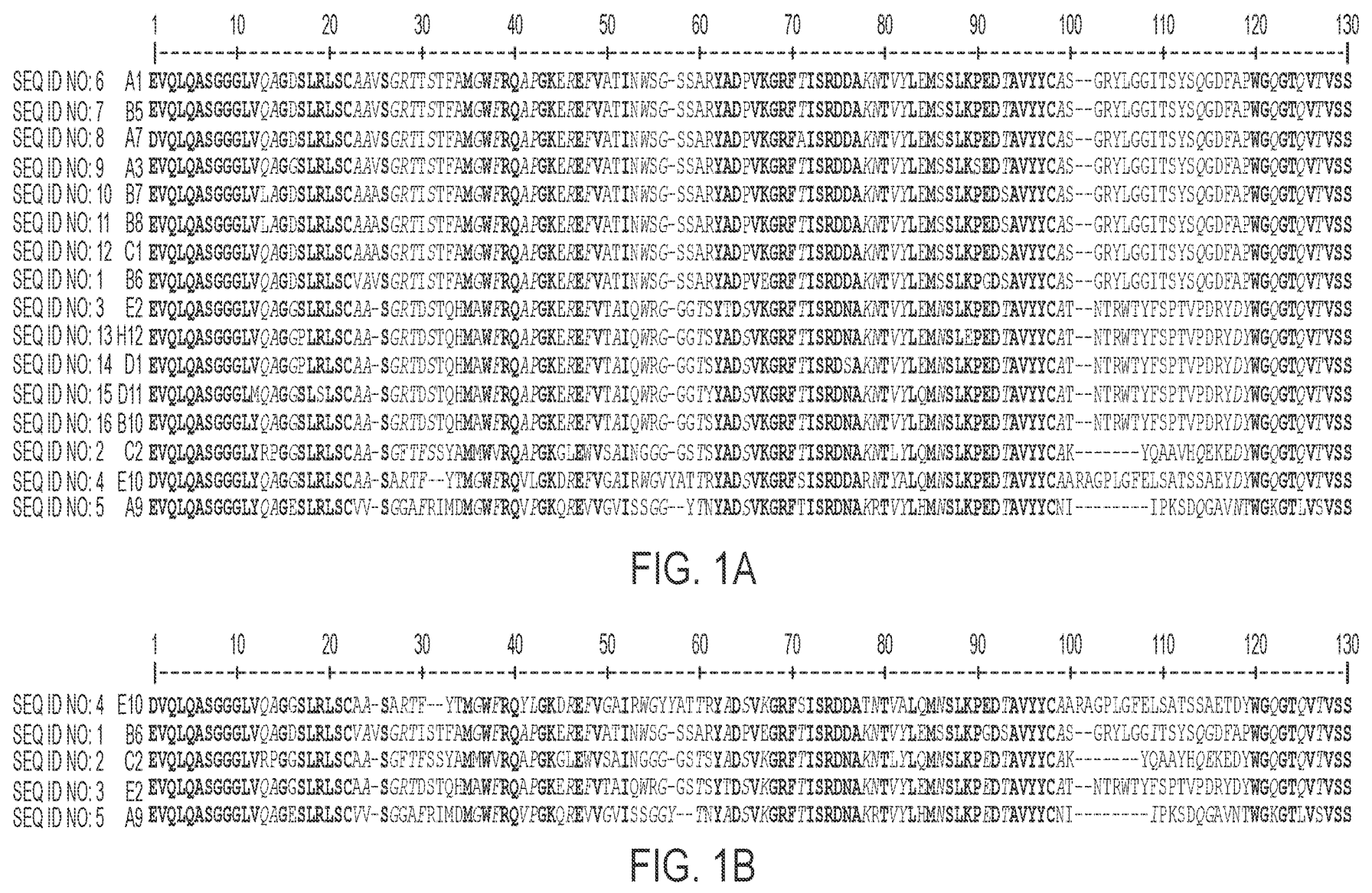

As referred to herein, the complementarity determining regions (CDRs) identified as CDR1, CDR2, and CDR3 are as follows, using the numbering scheme in the sequence alignment depicted FIG. 1A: CDR1 is the region of amino acid residues 26-35, CDR 2 is the region of amino acid residues 50-65, and CDR3 is the region of amino acid residues 99-119. These regions are inclusive of the endpoints.

As used herein, unless the context otherwise indicates, the terms "antibody" or "sdAb" include bivalent fusions of sdAbs.

Overview

Five sequence families of anti-SARS-CoV-2 N sdAb were selected from the immune phage display library prepared from a llama who had been immunized with recombinant SARS-CoV-2 nucleocapsid protein. Sequence families are defined as a group of sdAb sharing near-identical CDRs. The SARS-CoV-2 N specific binders were isolated by a biopanning procedure on immobilized SARS-CoV-2 N. Then, selected sequences were subcloned for protein preparation. A subset of prepared sdAb were then subjected to the binding assays and found to be positive for binding SARS-CoV-2 N by MagPlex® assay. In addition, their binding affinities were determine by surface plasmon resonance (SPR). Further specifics can be found in Anal. Chem. 2021, 93, 19, 7283-7291.

Examples

A llama was immunized four times with 100 µg of N protein and a high titer of serum was then obtained. RNA was extracted from buffy coats and cloned to a phage display vector to create a suitable library. A MagPlex® assay was used to evaluate 96 clones for binding to N, and from these, 16 were selected as those showing a strong signal. A sequence alignment of these is shown in FIG. 1A, with numbering based on the E10 sequence. From these, the five representative sequences having SEQ ID NOs: 1 through 5 were selected for further study—FIG. 1B provides their sequence alignment.

In general, sdAb sequences include three diverse complementarity determining regions (CDRs) and four conserved framework regions (FRs). As referred to here, CDR1 is defined as region of amino acid residues 26-35, CDR 2 as residues 50-65, and CDR3 as residues 99-119 using the numbering of the sequence alignment depicted FIGS. 1A and 1B.

Genetically linked bivalent sdAbs were also prepared using a strategy in which the first sdAb is flanked by NcoI-NotI restriction sites and the second sdAb is flanked by BamHI-XhoI restriction sites with a "GGGGSGGGGSGGGGS" (SEQ ID NO: 17) linker between them. In this way, the sdAbs could be combined as desired by substituting the first or second sdAb component so that homobivalent and heterobivalent sdAb constructs could be produced and purified. Bivalent antibodies were tested using SPR affinity with results shown in Table 1 below.

Affinity determination of sdAb were made by surface plasmon resonance (SPR) were performed using the PROTEON XPR36 (Bio-Rad, Hercules, Calif.). Lanes of a general layer compact chip were individually coated with N covalently linked to the chip following the standard 1-ethyl-3-(3-dimethylaminopropyl) carbodiimide hydrochloride/N-hydroxysulfosuccinimide (sulfo-NHS) coupling chemistry available from the manufacturer. For these experiments, three lanes of the chip were coated with N in decreasing concentrations to ensure that the off rate was not being suppressed by rebinding after dissociation due to the ligand being present at too high a concentration on the surface. After the ligand was immobilized, the chip was rotated 90° to allow the binding of the sdAb to be tested at a range of concentrations simultaneously. The chip was then regenerated, and the next sdAb was evaluated. Binding kinetics of each antibody was tested at 25° C. by flowing six concentrations of each sdAb varying from 300 to 0 nM at 100 µL/min for 90 s over the antigen-coated chip and then monitoring dissociation for 600 s. The data were analyzed using a global Langmuir fit, and the standard error was always less than 10%, typically ~1%; variation between multiple tests of the same sample was less than a factor of 2. The results obtained were well within the working range of the instrument, with an association constant (ka) between $3 \times 10^3$ and $3 \times 10^6 M^{-1} s^{-1}$ and a dissociation constant between $1 \times 10^{-6}$ and $6 \times 10^{-1} s^{-1}$. E2, C2, and B6 all possess high affinity. E10 is lower and A9 did not show specific binding via this assay. SPR affinity data are provided in Table 1 below.

TABLE 1

SPR Affinity Determinations of Both Standard and Bivalent sdAbs
NSB refers to non-specific binding

| clone | $k_a$ (1/M s) | $k_d$ (1/S) | $K_D$ (nM) |
|---|---|---|---|
| A9 | NSB | NSB | NSB |
| E10 | $6.9 \times 10^4$ | $9.5 \times 10^{-4}$ | 14 |
| E2 | $3.5 \times 10^5$ | $2.7 \times 10^{-4}$ | 0.8 |
| C2 | $1.6 \times 10^5$ | $1.8 \times 10^{-4}$ | 1.1 |
| B6 | $1.9 \times 10^5$ | $3.0 \times 10^{-4}$ | 1.6 |
| C2-C2 | $2.7 \times 10^5$ | $3.9 \times 10^{-5}$ | 1.4 |
| E2-E2 | $6.6 \times 10^6$ | $3.4 \times 10^{-4}$ | 0.05 |
| E2-B6 | $1.4 \times 10^6$ | $3.7 \times 10^{-4}$ | 0.3 |
| E2-C2 | $2.4 \times 10^6$ | $2.9 \times 10^{-4}$ | 0.1 |
| C2-B6 | $2.7 \times 10^5$ | $1.6 \times 10^{-4}$ | 0.6 |

Specificity and an indication of affinity were appraised via the direct binding of the sdAb to SARS-COV-2 N recombinant protein immobilized on MagPlex® magnetic microspheres (Luminex, Austin, Tex., USA), with results shown in FIG. 2. The SARS-COV-2 N, along with RBD, was immobilized to unique sets of MagPlex® microspheres using the standard immobilization protocol provided by the manufacturer. To prepare the biotinylated (Bt) tracer reagent, 10-fold excess of EZ-LINK NHS-LC-LC-Biotin (Thermo Fisher Scientific) was added to 300 µg of each sdAb at 1 mg/mL for 30 min; excess biotin was removed using Zeba spin columns (Thermo Fisher Scientific). The absorbance at 280 nM was used to calculate the concentration of Bt-sdAb. Dilutions of each Bt-sdAb in PBSTB [PBS +0.05% TWEEN +0.1% bovine serum albumin (BSA)] were prepared in round-bottom polypropylene microtiter plates (VWR). The mixture of antigen-coated MagPlex® microspheres was added to the wells. The plate was washed using PBST while placed on a 96f magnet (BioTek, Winooski, Vt.), incubated with 5 µg/mL streptavidin-R-phycoerythrin ([SA-PE] Molecular Probes, Eugene, Oreg.) for 30 min, and then washed, and then binding was evaluated on the MAGPIX instrument (Luminex, Austin, Tex.). As can be seen in FIG. 2 and Table 1, both the direct-binding MagPlex® and SPR showed that clones E2, B6, and C2 outperformed both E10 and A9.

While direct-binding assays can assess binding ability and specificity, a number of antibody-based diagnostic assays require antibody reagents to operate in a sandwich format. Because clones E2, B6, and C2 (SEQ ID NOs: 3, 1, and 2, respectively) appeared to have the best binding characteristics of the five, studies focused on integrating them into a sandwich format.

Sandwich format MagPlex® bead assays were performed in order to demonstrate the ability of the sdAbs to act as both the capture and recognition reagent for the detection of N. For these assays, each sdAb was immobilized to a set of MagPlex® microspheres as described above and then tested for its ability to function as a capture antibody. Initial tests evaluated all the clones as both the immobilized capture and the Bt recognition molecule in the assay. To improve the limit of detection (LOD) for N, the same assay format was repeated using the hetero- and homobivalent constructs of the three sdAbs that performed best in previous testing. For the amplified LOD assay using the standard sdAb reagents, the N was diluted into PBST with 1 mg/mL BSA, as were all the other assay reagents, and then further diluted on a round-bottom polypropylene microtiter plate. Then, the sdAb-coated microspheres were added to provide a minimum of 50 microspheres for each set per well and incubated for 30 min. In most tests, assay process-control microspheres were included but not shown to simplify the graphs. (39) The plate was washed with PBST and incubated with the desired Bt-sdAb at 1 µg/mL for 30 min. To generate the fluorescent signal, the plate was washed and then incubated sequentially with 50 µL of SA-PE at 5 µg/mL in each well for 15 min, washed again, then incubated with 50 µL of Bt goat anti-streptavidin (Bt-goat-anti-SA) from Vector Laboratories (Burlingame, Calif.) at 1 µg/mL for 15 min, washed, and finally incubated with SA-PE as before. Then, the plate was washed a final time prior to being evaluated on the MAGPIX. A ratio of 2 for the signal/background was utilized as the LOD as this ratio provides a signal that assures a difference that is greater than 3 times the standard deviation (SD) of the mean of both the background and the data point considered significant. The assay for the LOD for N using the bivalent sdAb reagents was similar to the above protocol other than the fact that the incubation step with N was extended to 1 h and that the N and all subsequent reagents were diluted into a 1:1 mixture of PBST and LOWCROSS-BUFFER (Candor, Wangen, Germany), which had been previously observed to improve assay sensitivity.

Figure 3:
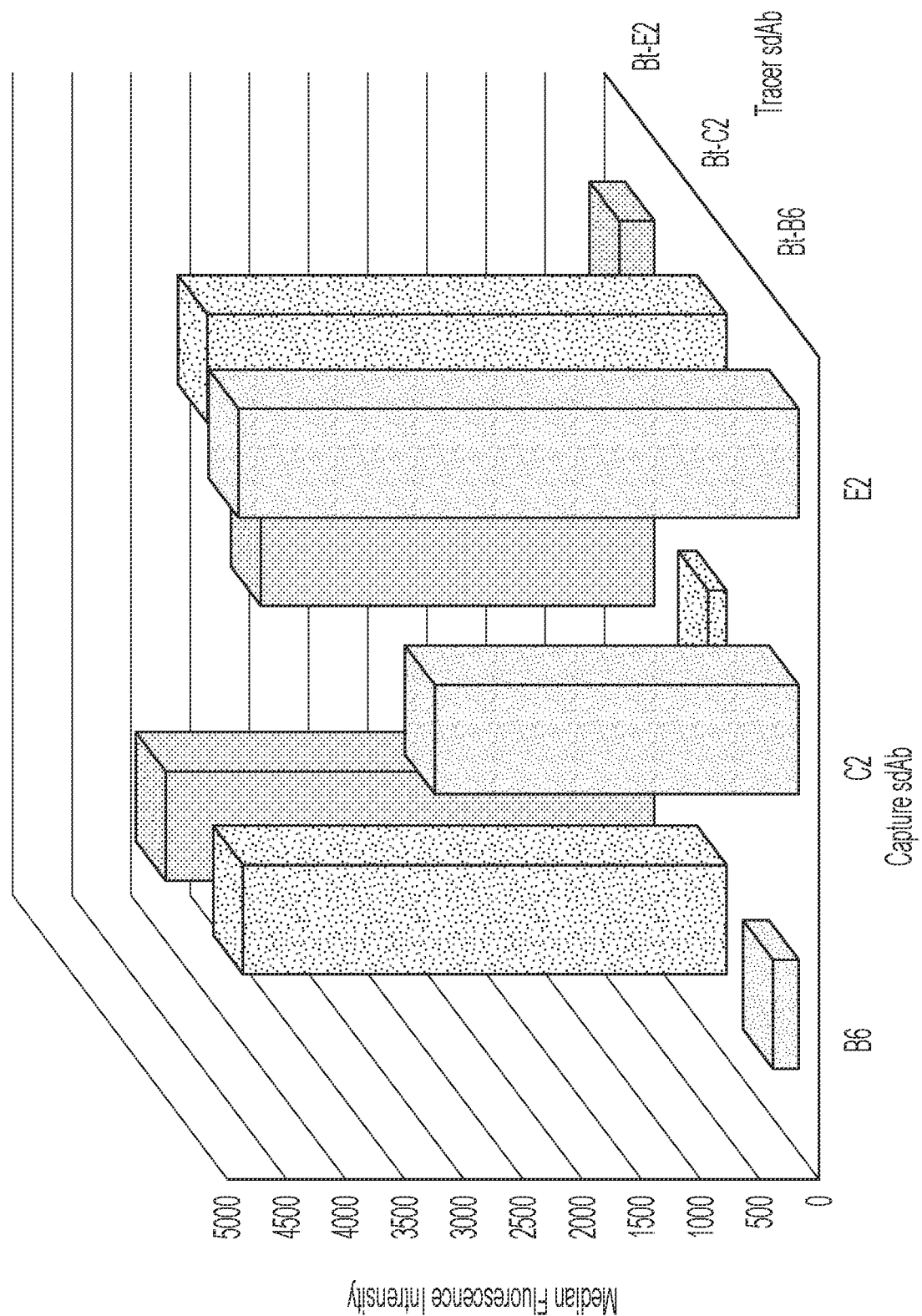
FIG. 3 displays a checkerboard format sandwich MagPlex® assay in which each of the three sdAbs is paired with itself and the other two. None of the sdAb captures works well with itself as a biotinylated (Bt) tracer, but each functions with the other two.

By immobilizing the sdAb onto microspheres, a checkerboard assay indicated that each of the clones E2, B6, and C2 binds to a distinct epitope on N (FIG. 3). Although native N is multimeric in nature, this data suggest that the recombinant N is monomeric as it can be seen that none of the sdAbs works efficiently as both capture and tracer; however, each can be paired with either of the other two.

Figure 4A:
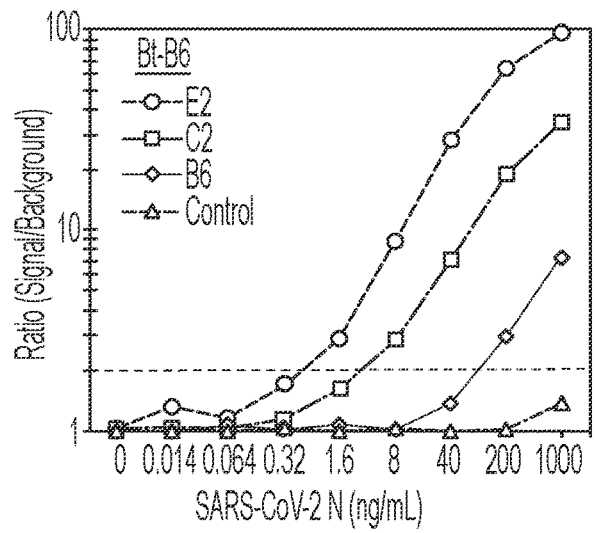
FIGS. 4A-4C present data from MagPlex® amplified sandwich fluid array assays for the detection of SARS-CoV-2 N using each sdAb as the Bt tracer with each sdAb on a separate capture microsphere set. The control shown was a MagPlex® set coated with sdAb toward an unrelated target. The assay was done in an amplified format, with a ratio of 2 (signals divided by background) being considered the limit of detection (LOD). Bt-tracer—A: Bt-B6, B: Bt-C2, and C: Bt-E2
Figure 4B:
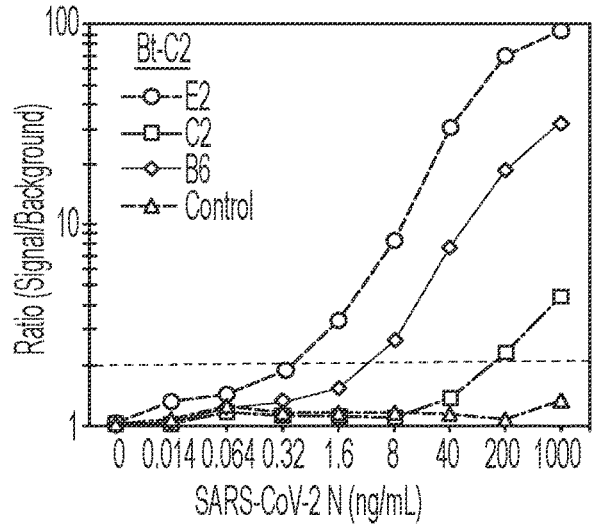
Figure 4C:
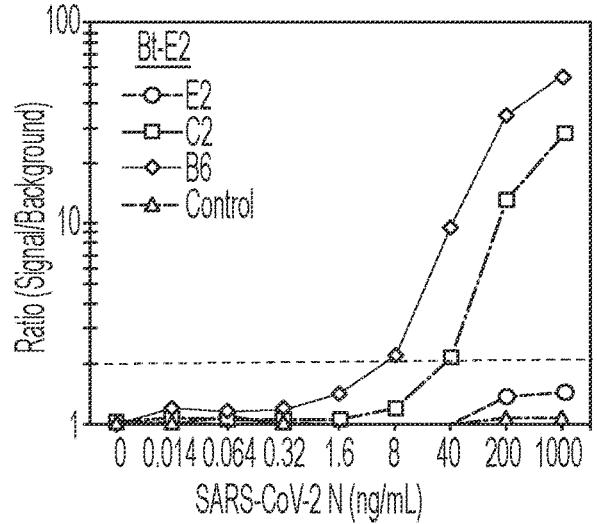

FIGS. 4A-4C provide dose-response curves to assess detection limits with the different sdAb pairs. This revealed that E2 was the best capture, providing detection down to about 1 ng/mL when paired with either B6 or C2 as tracers.

Multivalent sdAbs have proven superior to standard sdAbs for the neutralization of several viruses including SARS-CoV-2. Multivalent sdAbs can provide increased apparent affinity through avidity, making them advantageous for use in detection assays, and improved detection of several targets incorporating multivalent capture reagents has been observed. As the E2 was the best capture and recognizes a different epitope than C2 and B6, a bivalent version of E2 was prepared as well as combinations of E2 with C2 and B6 and a combination of C2 with B6. Also prepared was a C2-C2 construct to determine if the bivalent version would prove to be a better capture reagent. Direct-binding MagPlex® assays showed that the E2-B6 and E2-C2 heterobivalent constructs were much better than the standard sdAbs, while the other constructs did not perform much different in this format. Analysis by SPR (Table 1) showed that with the exception of C2-C2, the other bivalent constructs all had sub-nM affinity for N, thus achieving the avidity, an apparent enhanced affinity, which was desired.

Figure 5:
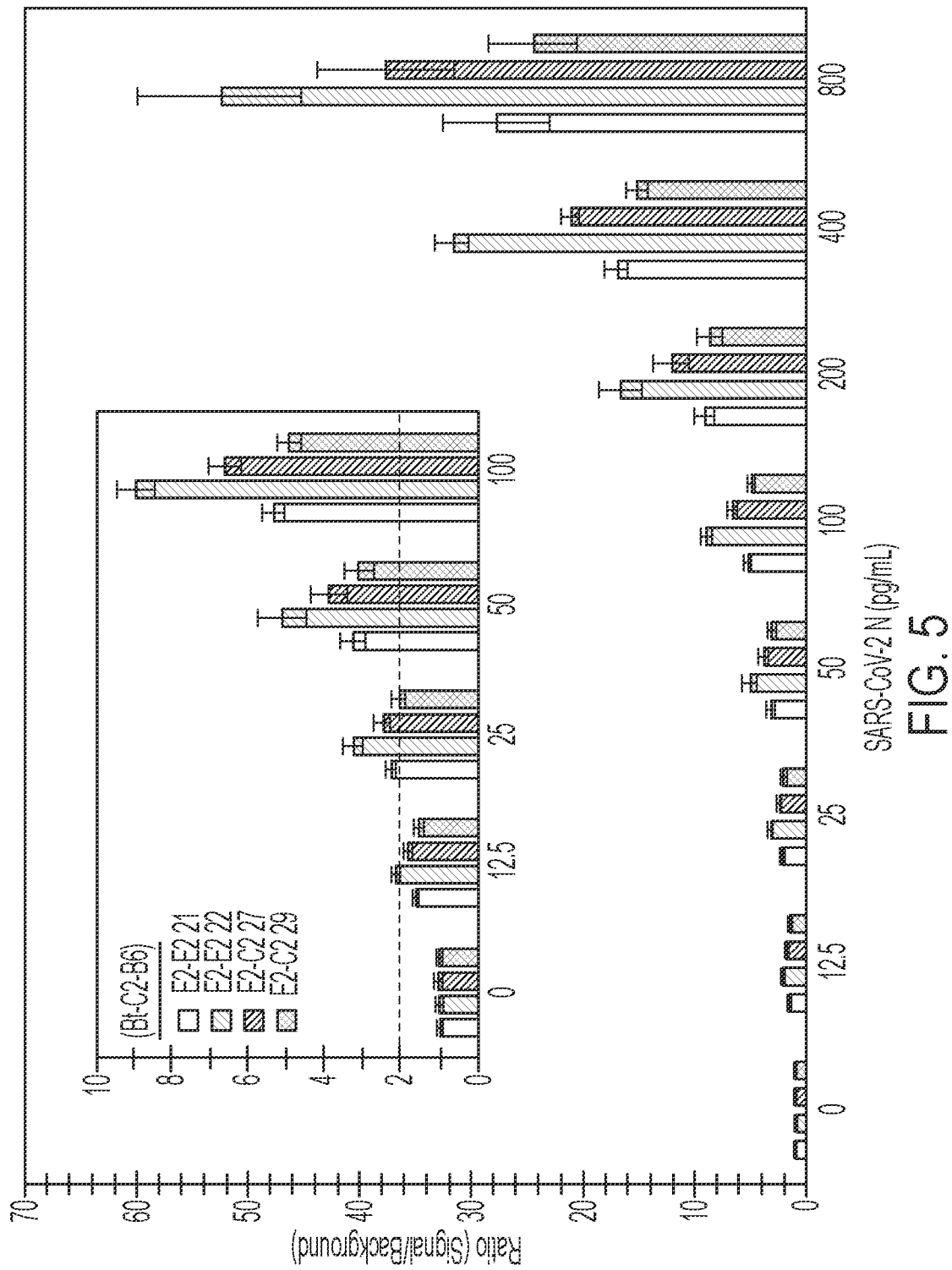
FIG. 5 shows results from a MagPlex® sandwich fluid array assay for the detection of SARS-CoV-2 N using two sets of E2-E2 and E2-C2 as the capture on the MagPlex® bead indicated in the legend and Bt-C2-B6 as the tracer in an amplified assay. A dose-response bar graph for an experiment conducted with eight replicates at each concentration is shown; error bars represent the SD of those eight replicates. This experiment was repeated three times, once as shown, once in quadruplicate, and once in triplicate, all giving similar results. A ratio of 2 (signal divided by a background) is considered the LOD.
Figure 6:
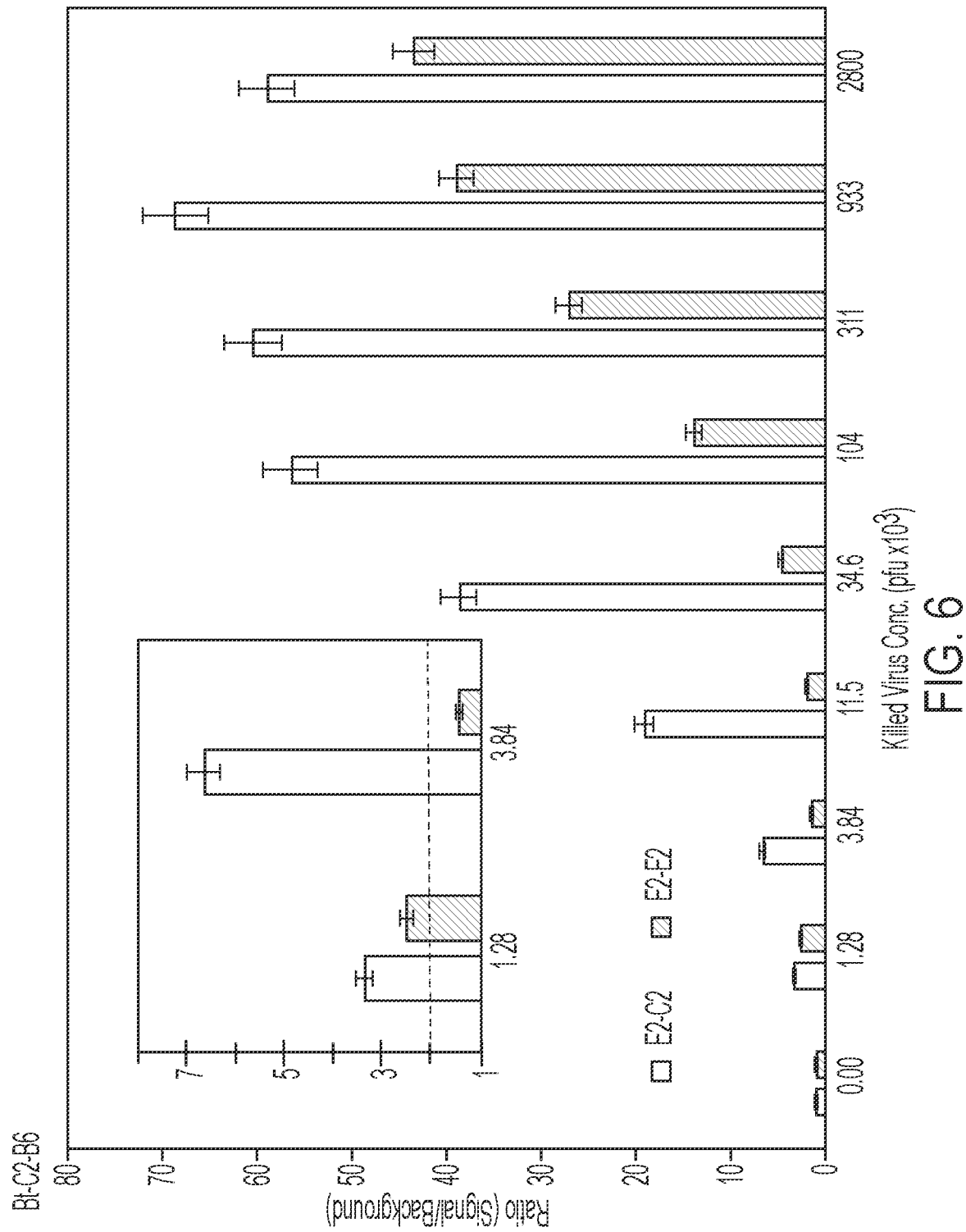
FIG. 6 provides data for a MagPlex® amplified sandwich immunoassay for the detection of killed SARS-CoV-2 virus using the E2-C2 and E2-E2 captures paired with the Bt-C2-B6 tracer. The inset shows the two lowest concentrations to allow visualization of the LOD. The error bars shown represent the average % CV of the data.
Figure 7A:
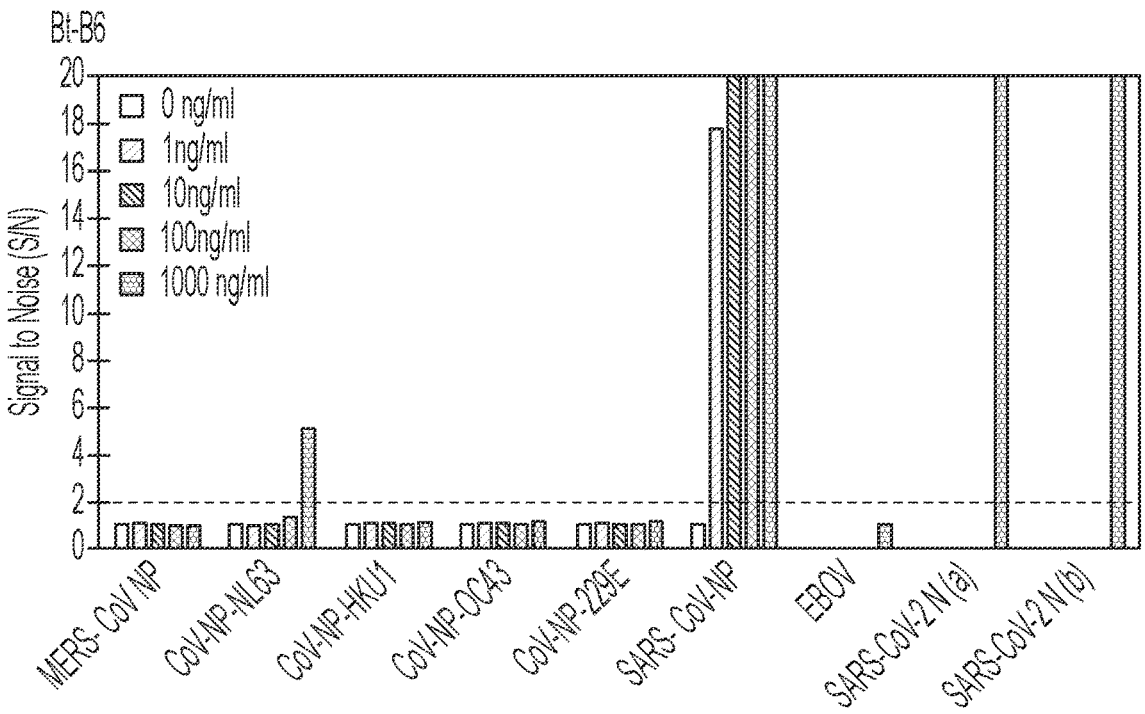
FIGS. 7A-7D provide results from a MagPlex® sandwich fluid array assay for the cross reactivity of the sdAb reagents. Shown is the assay using the E2-C2 capture and B6, E2, C2, and C2-B6 as indicated as the Bt tracer reagent. NP-NL63 is a truncation including aa 221-340. The two positive controls are recombinant SARS-CoV-2 N from two different sources, termed N (a) and N (b). N (a) was acquired from ACROBiosystems (Newark, Del., USA) while that termed SARS-CoV-2 N (b) was acquired from East Coast Bio (North Berwick, Me., USA)
Figure 7B:
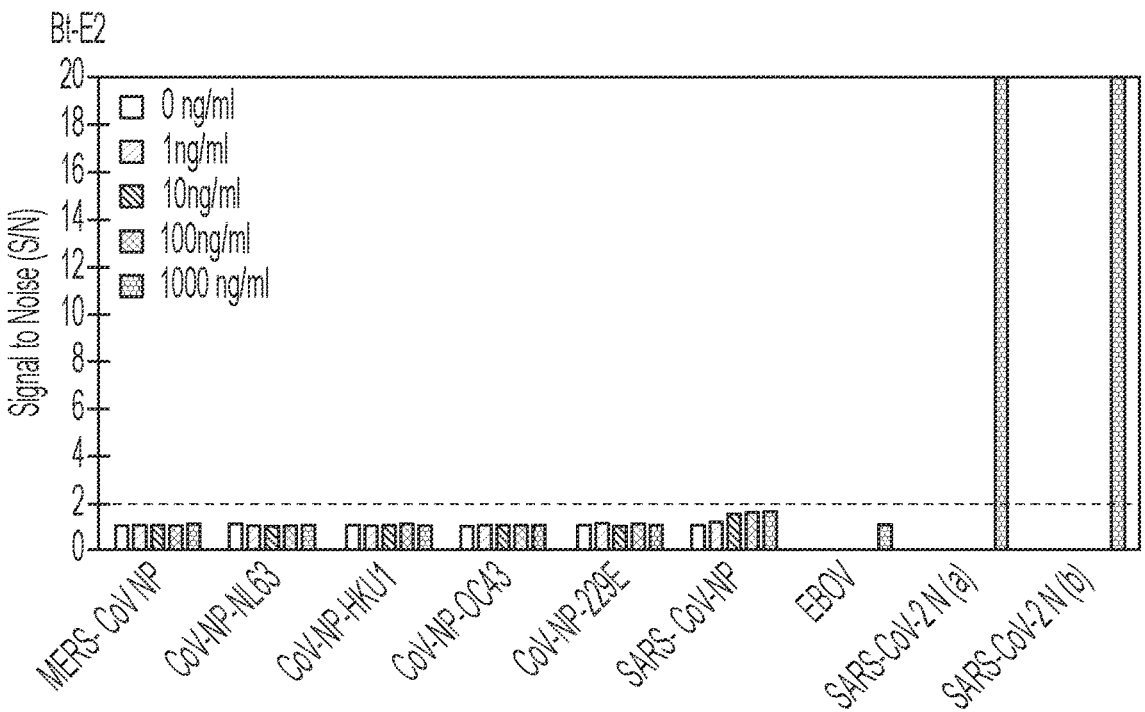
Figure 7C:
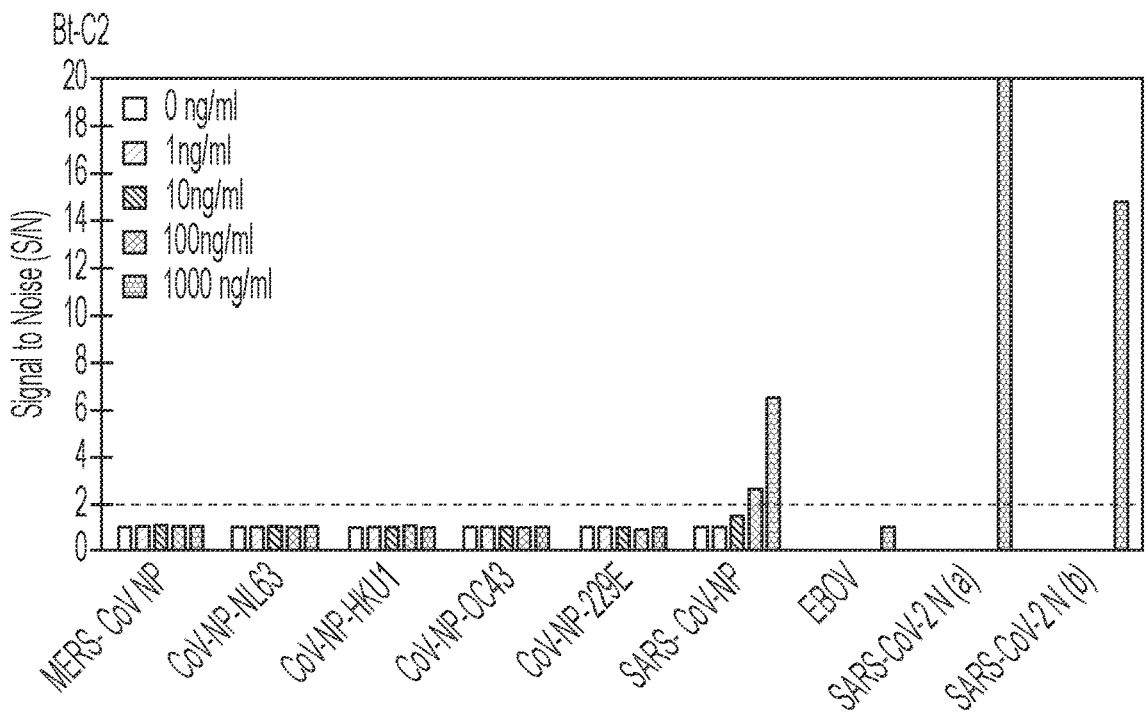
Figure 7D:
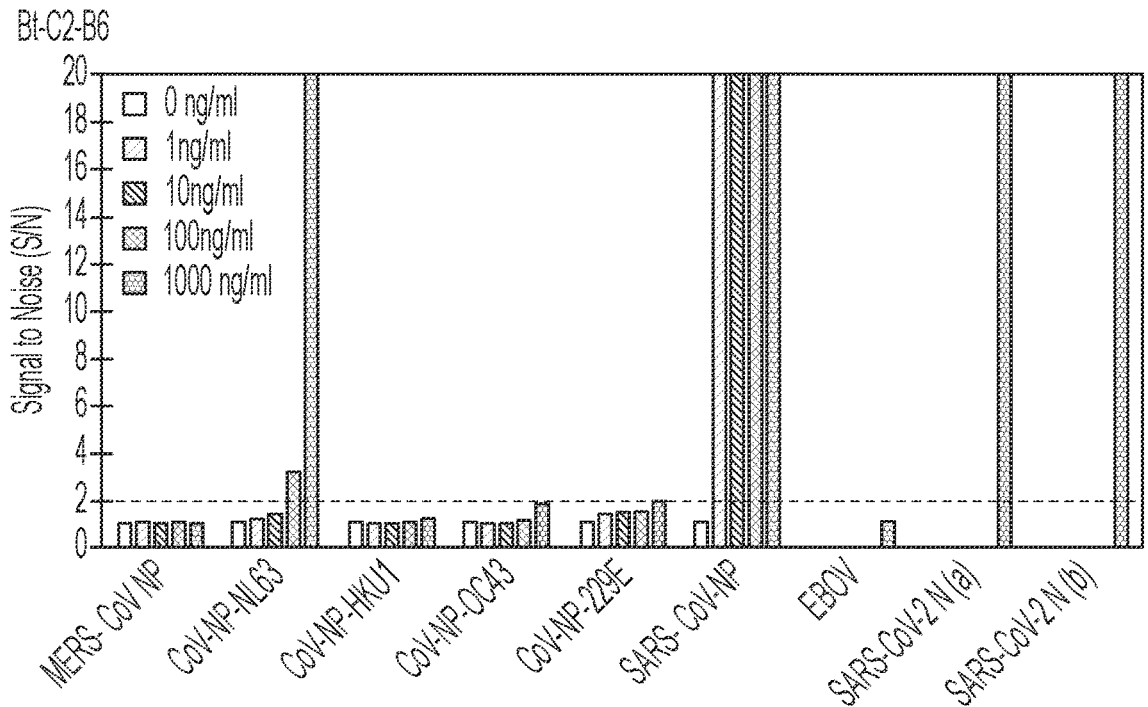

The bivalent sdAbs were incorporated into sandwich assays as both capture and tracer reagents. The E2-E2 and E2-C2 captures in conjunction with the Bt-C2-B6 tracer yielded the best results; dose-response curves were evaluated in preliminary experiments for all the reagents. To achieve consistent high sensitivity, a two-step amplification was employed where the initial signal generated by SA-PE is amplified by the addition of a layer of Bt-goat anti-SA, followed by a second layer of SA-PE. This amplification method has been found to provide little advantage for conventional antibodies but has shown to improve MagPlex® assays using sdAbs by a factor of 5 or better. Using this protocol, a LOD for N of 50 pg/mL was obtained (FIG. 5). This same assay was evaluated for the detection of the killed virus where all the viral components are present; a LOD of $1.28 \times 10^3$ pfu/mL killed virus was obtained using E2-C2 as the capture reagent (FIG. 6). These LODs suggest that this method may be successful for the detection of SARS-CoV-2 in actual patient samples.

Figure 8:
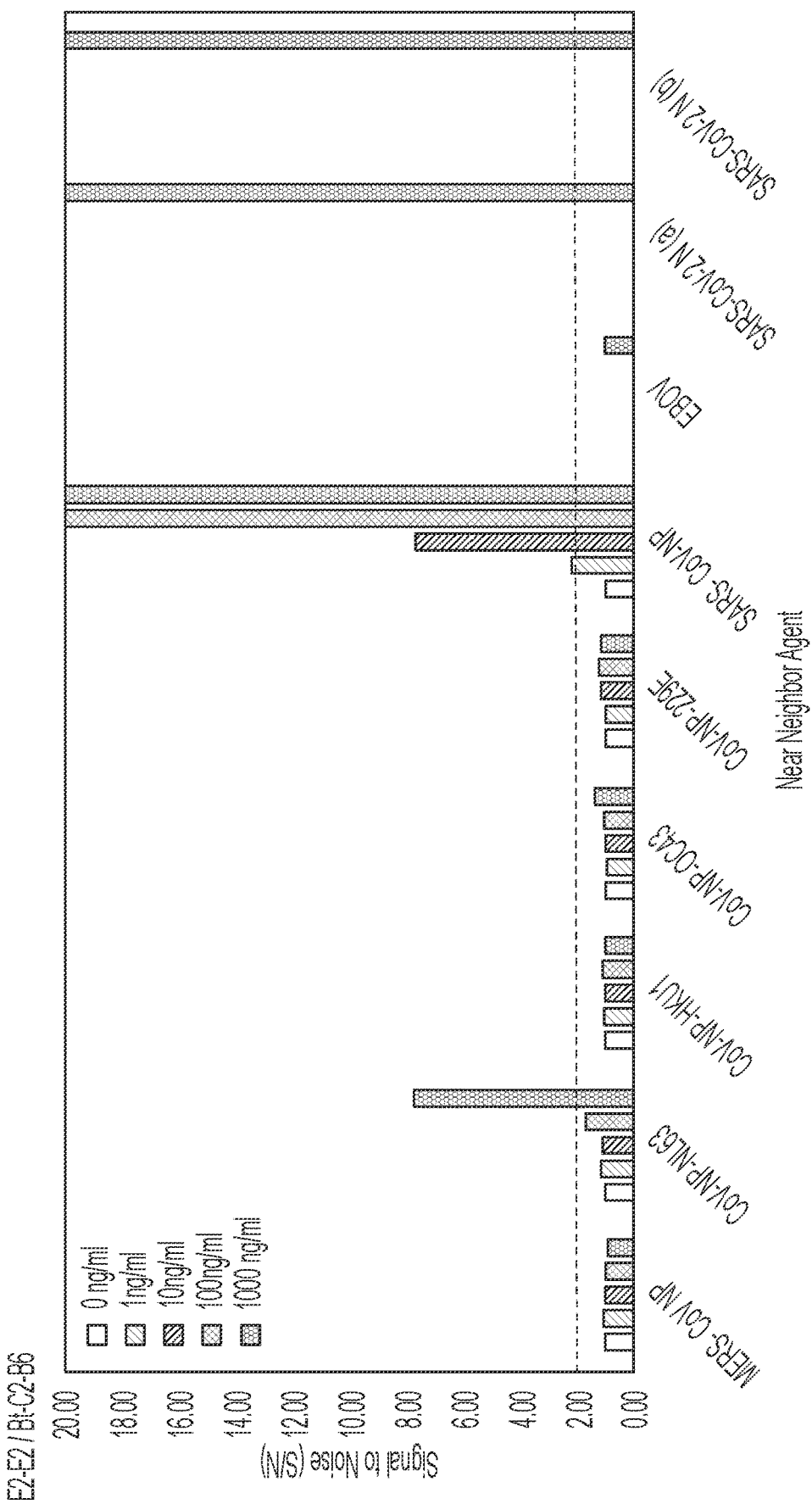
FIG. 8 shows the results with the E2-E2 capture and the Bt-C2-B6 tracer.

The cross reactivity of these reagents was also investigated. MagPlex® microspheres coated with E2, C2, B6, E2-E2, and E2-C2 were combined and tested simultaneously with each as the Bt tracer antibody. Since E2-C2 was functional as a capture for each of the Bt sdAb used as the tracer antibody, only that set is shown in FIG. 7. FIG. 8 shows the results with the E2-E2 capture and the Bt-C2-B6 tracer; additional data are not shown as the data presented provided the illuminating findings. The tracers that included B6 have strong cross reactivity to SARS-CoV N; otherwise, these reagents show good selectivity with cross reactivity to the other NP variants observed only at high concentrations. It is not surprising to observe cross reactivity with the SARS-CoV N as high similarity (over 87%) has been noted between the N sequence of SARS-CoV-2 and the N sequence of other β coronaviruses (i.e., SARS-CoV). As both of these coronaviruses can be associated with severe diseases, this cross reactivity should not be a liability for an assay built with the sdAbs, especially as MagPlex® assays can easily be multiplexed. It appears that E2 has much better selectivity than the other sdAbs, so it would be possible to detect and discriminate both SARS-CoV and SARS-CoV-2 simultaneously using multiple capture bead sets. This is confirmed in FIG. 8, where the response to SARS-CoV NP was much less for E2-E2 as the capture molecule than that was observed for E2-C2 in FIG. 7.

Further Embodiments

It is expected that these antibodies and their derivatives could be used in diagnostic assays. For example, a sample known or suspected to contain SARS-CoV-2 could be contacted with a bound or immobilized antibody that includes a protein sequence as described herein under conditions that permit antigen binding thereto. After rinsing the antibody-antigen complex to remove unbound components, wherein at least a portion of any SARS-CoV-2 N in the sample remains bound to the antibody, a response indicative of the presence of SARS-CoV-2 in the sample can be obtained by addition of a second anti-N antibody tagged with biotin that can be recognized by streptavidin-phycoerythrin for completion of a sandwich fluoroimmunoassay. Numerous alternative assay formats known in the art could be realized in order to obtain a signal indicating antigen binding to antibodies as described herein. They include surface plasmon resonance, MagPlex® fluorimmunoassay, enzyme-linked immunosorbent assays (ELISA), and the like. Suitable antibodies for these diagnostics could include any antibodies described, including monovalent and multivalent forms and variations thereof. In various aspects, the diagnostic assay could return a result signal indicating presence of SARS-CoV-2 when a limit of detection is reached or exceeded.

Modifications of the above-described examples are contemplated based on the sequences depicted in FIG. 1A. Variants might be programmatically generated, synthesized, and tested for binding using techniques known in the art. Moreover, any two individual sdAb, the same or different, could be joined through a polypeptide linker. It would also be possible to join more than two sdAb together to be expressed as a single fusion protein, for example three, four, five, or even more.

Polypeptide linkers could be shorter or longer than those used in the examples; for instance a linker might be 1 to 50 amino acids in length, inclusive. The length of the linker can be tuned by routine experimentation. It is expected that linkers comprising primarily glycine and serine will function as desired. Thus contemplated are linkers comprising at least 50% glycine and/or serine.

Furthermore, one or more sdAb can be joined to another protein in order to provide further functionality. For example, the sdAb(s) could be linked to an enzyme or fluorescent protein to aid in detection assays, and/or to a protein domain (e.g., albumin binding domain) that would enable an increased serum half-life that could be important for therapeutic use. Such joining could be accomplished through the expression of a fusion protein (optionally including a linker as noted above) or through post-translational joining.

For administration to subjects, such as humans, one may employ pharmaceutical compositions comprising one or more antibodies and a pharmaceutically acceptable carrier or excipient. In the present context, the term "pharmaceutically acceptable" means that the carrier or excipient, at the dosages and concentrations employed, will not cause any unwanted or harmful effects in the subjects to that they are administered. Such pharmaceutically acceptable carriers and excipients are well known in the art. The preferably are formulated and administered as a sterile solution, although it may also be possible to utilize lyophilized preparations. Sterile solutions are prepared by sterile filtration or by other methods known per se in the art. The solutions are then lyophilized or filled into pharmaceutical dosage containers. The pH of the solution generally is in the range of pH 3.0 to 9.5, e.g., pH 5.0 to 7.5. The antibodies typically are in a solution having a suitable pharmaceutically acceptable buffer, and the composition may also contain a salt. Optionally, stabilizing agent may be present, such as albumin. In certain embodiments, detergent is added. In certain embodiments, the antibodies may be formulated into an injectable preparation.

Compositions may be administered to a subject, e.g., a human subject. The total dose of anti-N antibodies in a composition for a single administration can, for instance, be about 0.01 µg to much greater levels. Expected human dosages might be in the rage of about 100 mg to about 5 grams. Determining the recommended dose will be carried out by experimentation and is routine for those skilled in the art Administration of the compositions according to the disclosure can be performed using standard routes of administration. Non-limiting embodiments include parenteral administration, such as intradermal, intramuscular, subcutaneous, transcutaneous, or mucosal administration, e.g., intranasal, oral, and the like. In one embodiment, a composition is administered by intramuscular injection.

It is possible that one or more of the sdAb described herein could serve as therapeutics for the treatment of COVID-19. Thus, contemplated herein are medicaments comprising one or more of these sdAb in conjunction with a pharmaceutically-acceptable carrier. Also contemplated are methods of treatment comprising administering such a medicament to a patient in need thereof.

Advantages

SdAb are small recombinant molecules that can be produced easily and economically. In addition, they can easily be prepared as fusion constructs that can endow them with additional properties in a controlled manner. Most importantly, in comparison with polyclonal antibodies, sdAb are a consistent, known entity, and unlike most monoclonal antibodies which are derived from a cell line where the actual antibody has not been sequenced, all the information need to reproduce the sdAb is provided in it relatively short amino acid sequence. These factors along with their high affinity and specificity make sdAb ideal reagents for use in diagnostics for SARS-CoV-2 nucleocapsid protein and any future therapeutic application as well.

CONCLUDING REMARKS

All documents mentioned herein are hereby incorporated by reference for the purpose of disclosing and describing the particular materials and methodologies for which the document was cited.

Although the present invention has been described in connection with preferred embodiments thereof, it will be appreciated by those skilled in the art that additions, deletions, modifications, and substitutions not specifically described may be made without departing from the spirit and scope of the invention. Terminology used herein should not be construed as being "means-plus-function" language unless the term "means" is expressly used in association therewith.

REFERENCES

1. Lu R., Zhao X., Li J., Niu P., Yang B., Wu H., Wang W, Song H., Huang B., Zhu N., Bi Y, Ma X., Zhan F., Wang L., Hu T., Zhou H., Hu Z., Zhou W, Zhao L., Chen J., Meng Y, Wang J., Lin Y, Yuan J., Xie Z., Ma J., Liu W. J., Wang D., Xu W, Holmes E. C., Gao G. F., Wu G., Chen W, Shi W, Tan W. Genomic characterisation and epidemiology of 2019 novel coronavirus: implications for virus origins and receptor binding. Lancet (London, England) 2020; 395:565-574.
2. Shang B., Wang X. Y., Yuan J. W., Vabret A., Wu X. D., Yang R. F., Tian L., Ji Y Y, Deubel V., Sun B. Characterization and application of monoclonal antibodies against N protein of SARS-coronavirus. Biochem. Biophys. Res. Commun. 2005; 336:110-117
3. Liu S. J., Leng C. H., Lien S. P., Chi H. Y., Huang C. Y., Lin C. L., Lian W C., Chen C. J., Hsieh S. L., Chong P. Immunological characterizations of the nucleocapsid protein based SARS vaccine candidates. Vaccine. 2006; 24:3100-3108.
4. Narayanan K., Chen C.-J., Maeda J., Makino S. Nucleocapsid-independent specific viral RNA packaging via viral envelope protein and viral RNA signal. J. Virol. 2003; 77:2922-2927.
5. Hurst K. R., Koetzner C. A., Masters P. S. Identification of in vivo-interacting domains of the murine coronavirus nucleocapsid protein. J. Virol. 2009; 83:7221-7234.
6. Huang Q., Yu L., Petros A. M., Gunasekera A., Liu Z., Xu N., Hajduk P., Mack J., Fesik S. W., Olejniczak E. T. Structure of the N-terminal RNA-binding domain of the SARS CoV nucleocapsid protein. Biochemistry. 2004; 43:6059-6063.
7. Saikatendu K. S., Joseph IS., Subramanian V., Neuman B. W., Buchmeier M. J., Stevens R. C., Kuhn P. Ribonucleocapsid formation of severe acute respiratory syndrome coronavirus through molecular action of the N-terminal domain of N protein. J. Virol. 2007; 81:3913-3921.

8. Chen C. Y., Chang C. K., Chang Y. W., Sue S. C., Bai H. I., Riang L., Hsiao C. D., Huang T. H. Structure of the SARS coronavirus nucleocapsid protein RNA-binding dimerization domain suggests a mechanism for helical packaging of viral RNA. J. Mol. Biol. 2007; 368:1075-1086.
9. He R., Dobie F., Ballantine M., Leeson A., Li Y, Bastien N., Cutts T., Andonov A., Cao J., Booth T. F., Plummer F. A., Tyler S., Baker L., Li X. Analysis of multimerization of the SARS coronavirus nucleocapsid protein. Biochem. Biophys. Res. Commun. 2004; 316:476-483.
10. Chang C.-k., Chen C.-M. M., Chiang M.-h., Hsu Y-l., Huang T.-h. Transient oligomerization of the SARS-CoV N protein—implication for virus ribonucleoprotein packaging. PloS One. 2013; 8
11. Zeng W, Liu G, Ma H, et al. Biochemical characterization of SARS-CoV-2 nucleocapsid protein. Biochem Biophys Res Commun. 2020; 527(3):618-623. doi:10.1016/j.bbrc.2020.04.136
12. Sabino-Silva, R., A. C. G. Jardim, and W. L. Siqueira, Coronavirus COVID-19 impacts to dentistry and potential salivary diagnosis. Clin Oral Investig, 2020.
13. Wang, Y., et al., Combination of RT-qPCR Testing and Clinical Features For Diagnosis of COVID-19 facilitates management of SARS-CoV-2 Outbreak. J Med Virol, 2020.
14. Zu, Z. Y., et al., Coronavirus Disease 2019 (COVID-19): A Perspective from China. Radiology, 2020: p. 200490.
15. Pan, F., et al., Time Course of Lung Changes On Chest CT During Recovery From 2019 Novel Coronavirus (COVID-19) Pneumonia. Radiology, 2020: p. 200370.
16. Che, X. Y., et al., Nucleocapsid protein as early diagnostic marker for SARS. Emerg Infect Dis, 2004. 10(11): p. 1947-9.

What is claimed is:

1. An isolated antibody comprising a protein sequence selected from the group consisting of SEQ ID NOs: 1, 2, 3, 4, 5, 6, 7, 8, 9, 10. 11, 12, 13, 14, 15, and 16.

2. The isolated antibody of claim 1, wherein the sequence is SEQ ID NO: 1, SEQ ID NO: 2, or SEQ ID NO: 3.

3. An isolated bivalent antibody comprising two antibodies according to claim 1, wherein the antibodies are connected by a polypeptide linker and the antibodies are the same or different.

4. An isolated nucleotide encoding an antibody selected from the group consisting of SEQ ID NOs: 1, 2, 3, 4, 5, 6, 7, 8, 9, 10, 11, 12, 13, 14, 15, and 16.

* * * * *

SEQUENCE LISTING

```
<160> NUMBER OF SEQ ID NOS: 17

<210> SEQ ID NO 1
<211> LENGTH: 127
<212> TYPE: PRT
<213> ORGANISM: Lama glama

<400> SEQUENCE: 1

Glu Val Gln Leu Gln Ala Ser Gly Gly Gly Leu Val Gln Ala Gly Asp
1               5                   10                  15

Ser Leu Arg Leu Ser Cys Val Ala Val Ser Gly Arg Thr Ile Ser Thr
            20                  25                  30

Phe Ala Met Gly Trp Phe Arg Gln Ala Pro Gly Lys Glu Arg Glu Phe
        35                  40                  45

Val Ala Thr Ile Asn Trp Ser Gly Ser Ser Ala Arg Tyr Ala Asp Pro
    50                  55                  60

Val Glu Gly Arg Phe Thr Ile Ser Arg Asp Asp Ala Lys Asn Thr Val
65                  70                  75                  80

Tyr Leu Glu Met Ser Ser Leu Lys Pro Gly Asp Ser Ala Val Tyr Tyr
                85                  90                  95

Cys Ala Ser Gly Arg Tyr Leu Gly Gly Ile Thr Ser Tyr Ser Gln Gly
            100                 105                 110

Asp Phe Ala Pro Trp Gly Gln Gly Thr Gln Val Thr Val Ser Ser
        115                 120                 125

<210> SEQ ID NO 2
<211> LENGTH: 121
<212> TYPE: PRT
<213> ORGANISM: Lama glama

<400> SEQUENCE: 2

Glu Val Gln Leu Gln Ala Ser Gly Gly Gly Leu Val Arg Pro Gly Gly
1               5                   10                  15

Ser Leu Arg Leu Ser Cys Ala Ala Ser Gly Phe Thr Phe Ser Ser Tyr
            20                  25                  30

Ala Met Met Trp Val Arg Gln Ala Pro Gly Lys Gly Leu Glu Trp Val
        35                  40                  45

Ser Ala Ile Asn Gly Gly Gly Ser Thr Ser Tyr Ala Asp Ser Val
    50                  55                  60

Lys Gly Arg Phe Thr Ile Ser Arg Asp Asn Ala Lys Asn Thr Leu Tyr
```

```
                65                  70                  75                  80
Leu Gln Met Asn Ser Leu Lys Pro Glu Asp Thr Ala Val Tyr Tyr Cys
                    85                  90                  95

Ala Lys Tyr Gln Ala Ala Val His Gln Glu Lys Glu Asp Tyr Trp Gly
            100                 105                 110

Gln Gly Thr Gln Val Thr Val Ser Ser
        115                 120

<210> SEQ ID NO 3
<211> LENGTH: 126
<212> TYPE: PRT
<213> ORGANISM: Lama glama

<400> SEQUENCE: 3

Glu Val Gln Leu Gln Ala Ser Gly Gly Gly Leu Val Gln Ala Gly Gly
1               5                   10                  15

Ser Leu Arg Leu Ser Cys Ala Ala Ser Gly Arg Thr Asp Ser Thr Gln
            20                  25                  30

His Met Ala Trp Phe Arg Gln Ala Pro Gly Lys Glu Arg Glu Phe Val
        35                  40                  45

Thr Ala Ile Gln Trp Arg Gly Gly Thr Ser Tyr Thr Asp Ser Val
    50                  55                  60

Lys Gly Arg Phe Thr Ile Ser Arg Asp Asn Ala Lys Asn Thr Val Tyr
65                  70                  75                  80

Leu Glu Met Asn Ser Leu Lys Pro Glu Asp Thr Ala Val Tyr Tyr Cys
                85                  90                  95

Ala Thr Asn Thr Arg Trp Thr Tyr Phe Ser Pro Thr Val Pro Asp Arg
            100                 105                 110

Tyr Asp Tyr Trp Gly Gln Gly Thr Gln Val Thr Val Ser Ser
        115                 120                 125

<210> SEQ ID NO 4
<211> LENGTH: 127
<212> TYPE: PRT
<213> ORGANISM: Lama glama

<400> SEQUENCE: 4

Asp Val Gln Leu Gln Ala Ser Gly Gly Gly Leu Val Gln Ala Gly Gly
1               5                   10                  15

Ser Leu Arg Leu Ser Cys Ala Ala Ser Ala Arg Thr Phe Tyr Thr Met
            20                  25                  30

Gly Trp Phe Arg Gln Val Leu Gly Lys Asp Arg Glu Phe Val Gly Ala
        35                  40                  45

Ile Arg Trp Gly Val Tyr Ala Thr Thr Arg Tyr Ala Asp Ser Val Lys
    50                  55                  60

Gly Arg Phe Ser Ile Ser Arg Asp Asp Ala Thr Asn Thr Val Ala Leu
65                  70                  75                  80

Gln Met Asn Ser Leu Lys Pro Asp Thr Ala Val Tyr Tyr Cys Ala
                85                  90                  95

Ala Arg Ala Gly Pro Leu Gly Phe Glu Leu Ser Ala Thr Ser Ser Ala
            100                 105                 110

Glu Tyr Asp Tyr Trp Gly Gln Gly Thr Gln Val Thr Val Ser Ser
        115                 120                 125

<210> SEQ ID NO 5
<211> LENGTH: 119
<212> TYPE: PRT
```

```
<213> ORGANISM: Lama glama

<400> SEQUENCE: 5

Glu Val Gln Leu Gln Ala Ser Gly Gly Gly Leu Val Gln Ala Gly Glu
1               5                   10                  15

Ser Leu Arg Leu Ser Cys Val Val Ser Gly Ala Phe Arg Ile Met
            20                  25                  30

Asp Met Gly Trp Phe Arg Gln Val Pro Gly Lys Gln Arg Glu Val Val
                35                  40                  45

Gly Val Ile Ser Ser Gly Gly Tyr Thr Asn Tyr Ala Asp Ser Val Lys
        50                  55                  60

Gly Arg Phe Thr Ile Ser Arg Asp Asn Ala Lys Arg Thr Val Tyr Leu
65                  70                  75                  80

His Met Asn Ser Leu Lys Pro Glu Asp Thr Ala Val Tyr Tyr Cys Asn
                85                  90                  95

Ile Ile Pro Lys Ser Asp Gln Gly Ala Val Asn Thr Trp Gly Lys Gly
                100                 105                 110

Thr Leu Val Ser Val Ser Ser
            115

<210> SEQ ID NO 6
<211> LENGTH: 127
<212> TYPE: PRT
<213> ORGANISM: Lama glama

<400> SEQUENCE: 6

Glu Val Gln Leu Gln Ala Ser Gly Gly Gly Leu Val Gln Ala Gly Asp
1               5                   10                  15

Ser Leu Arg Leu Ser Cys Ala Ala Val Ser Gly Arg Thr Thr Ser Thr
            20                  25                  30

Phe Ala Met Gly Trp Phe Arg Gln Ala Pro Gly Lys Glu Arg Glu Phe
                35                  40                  45

Val Ala Thr Ile Asn Trp Ser Gly Ser Ser Ala Arg Tyr Ala Asp Pro
        50                  55                  60

Val Lys Gly Arg Phe Thr Ile Ser Arg Asp Asp Ala Lys Asn Thr Val
65                  70                  75                  80

Tyr Leu Glu Met Ser Ser Leu Lys Pro Glu Asp Thr Ala Val Tyr Tyr
                85                  90                  95

Cys Ala Ser Gly Arg Tyr Leu Gly Gly Ile Thr Ser Tyr Ser Gln Gly
                100                 105                 110

Asp Phe Ala Pro Trp Gly Gln Gly Thr Gln Val Thr Val Ser Ser
            115                 120                 125

<210> SEQ ID NO 7
<211> LENGTH: 127
<212> TYPE: PRT
<213> ORGANISM: Lama glama

<400> SEQUENCE: 7

Glu Val Gln Leu Gln Ala Ser Gly Gly Gly Leu Val Gln Ala Gly Asp
1               5                   10                  15

Ser Leu Arg Leu Ser Cys Ala Ala Val Ser Gly Arg Thr Thr Ser Thr
            20                  25                  30

Phe Ala Met Gly Trp Phe Arg Gln Ala Pro Gly Lys Glu Arg Glu Phe
                35                  40                  45

Val Ala Thr Ile Asn Trp Ser Gly Ser Ser Ala Arg Tyr Ala Asp Pro
        50                  55                  60
```

```
Val Lys Gly Arg Phe Thr Ile Ser Arg Asp Asp Ala Lys Asn Thr Val
 65                  70                  75                  80

Tyr Leu Glu Met Ser Ser Leu Lys Pro Glu Asp Thr Ala Val Tyr Tyr
                 85                  90                  95

Cys Ala Ser Gly Arg Tyr Leu Gly Gly Ile Thr Ser Tyr Ser Gln Gly
            100                 105                 110

Asp Phe Ala Pro Trp Gly Gln Gly Thr Gln Val Thr Val Ser Ser
        115                 120                 125

<210> SEQ ID NO 8
<211> LENGTH: 127
<212> TYPE: PRT
<213> ORGANISM: Lama glama

<400> SEQUENCE: 8

Asp Val Gln Leu Gln Ala Ser Gly Gly Gly Leu Val Gln Ala Gly Asp
 1               5                  10                  15

Ser Leu Arg Leu Ser Cys Ala Ala Val Ser Gly Arg Thr Ile Ser Thr
             20                  25                  30

Phe Ala Met Gly Trp Phe Arg Gln Ala Pro Gly Lys Glu Arg Glu Phe
         35                  40                  45

Val Ala Thr Ile Asn Trp Ser Gly Ser Ser Ala Arg Tyr Ala Asp Pro
     50                  55                  60

Val Lys Gly Arg Phe Ala Ile Ser Arg Asp Asp Ala Lys Asn Thr Val
 65                  70                  75                  80

Tyr Leu Glu Met Ser Ser Leu Lys Pro Glu Asp Thr Ala Val Tyr Tyr
                 85                  90                  95

Cys Ala Ser Gly Arg Tyr Leu Gly Gly Ile Thr Ser Tyr Ser Gln Gly
            100                 105                 110

Asp Phe Ala Pro Trp Gly Gln Gly Thr Gln Val Thr Val Ser Ser
        115                 120                 125

<210> SEQ ID NO 9
<211> LENGTH: 127
<212> TYPE: PRT
<213> ORGANISM: Lama glama

<400> SEQUENCE: 9

Glu Val Gln Leu Gln Ala Ser Gly Gly Gly Leu Val Gln Ala Gly Gly
 1               5                  10                  15

Ser Leu Arg Leu Ser Cys Ala Ala Val Ser Gly Arg Thr Thr Ser Thr
             20                  25                  30

Phe Ala Met Gly Trp Phe Arg Gln Ala Pro Gly Lys Glu Arg Glu Phe
         35                  40                  45

Val Ala Thr Ile Asn Trp Ser Gly Ser Ser Ala Arg Tyr Ala Asp Pro
     50                  55                  60

Val Lys Gly Arg Phe Thr Ile Ser Arg Asp Asp Ala Lys Asn Thr Val
 65                  70                  75                  80

Tyr Leu Glu Met Ser Ser Leu Lys Ser Glu Asp Thr Ala Val Tyr Tyr
                 85                  90                  95

Cys Ala Ser Gly Arg Tyr Leu Gly Gly Ile Thr Ser Tyr Ser Gln Gly
            100                 105                 110

Asp Phe Ala Pro Trp Gly Gln Gly Thr Gln Val Thr Val Ser Ser
        115                 120                 125

<210> SEQ ID NO 10
```

-continued

```
<211> LENGTH: 127
<212> TYPE: PRT
<213> ORGANISM: Lama glama

<400> SEQUENCE: 10
```

Glu Val Gln Leu Gln Ala Ser Gly Gly Gly Leu Val Leu Ala Gly Asp
1               5                   10                  15

Ser Leu Arg Leu Ser Cys Ala Ala Ser Gly Arg Thr Ile Ser Thr
            20                  25                  30

Phe Ala Met Gly Trp Phe Arg Gln Ala Pro Gly Lys Glu Arg Glu Phe
        35                  40                  45

Val Ala Thr Ile Asn Trp Ser Gly Ser Ser Ala Arg Tyr Ala Asp Pro
50                  55                  60

Val Lys Gly Arg Phe Thr Ile Ser Arg Asp Asp Ala Lys Asn Thr Val
65                  70                  75                  80

Tyr Leu Glu Met Ser Ser Leu Lys Pro Glu Asp Ser Ala Val Tyr Tyr
                85                  90                  95

Cys Ala Ser Gly Arg Tyr Leu Gly Gly Ile Thr Ser Tyr Ser Gln Gly
            100                 105                 110

Asp Phe Ala Pro Trp Gly Gln Gly Thr Gln Val Thr Val Ser Ser
        115                 120                 125

```
<210> SEQ ID NO 11
<211> LENGTH: 127
<212> TYPE: PRT
<213> ORGANISM: Lama glama

<400> SEQUENCE: 11
```

Glu Val Gln Leu Gln Ala Ser Gly Gly Gly Leu Val Leu Ala Gly Asp
1               5                   10                  15

Ser Leu Arg Leu Ser Cys Ala Ala Ser Gly Arg Thr Ile Ser Thr
            20                  25                  30

Phe Ala Met Gly Trp Phe Arg Gln Ala Pro Gly Lys Glu Arg Glu Phe
        35                  40                  45

Val Ala Thr Ile Asn Trp Ser Gly Ser Ser Ala Arg Tyr Ala Asp Pro
50                  55                  60

Val Lys Gly Arg Phe Thr Ile Ser Arg Asp Asp Ala Lys Asn Thr Val
65                  70                  75                  80

Tyr Leu Glu Met Ser Ser Leu Lys Pro Glu Asp Ser Ala Val Tyr Tyr
                85                  90                  95

Cys Ala Ser Gly Arg Tyr Leu Gly Gly Ile Thr Ser Tyr Ser Gln Gly
            100                 105                 110

Asp Phe Ala Pro Trp Gly Gln Gly Thr Gln Val Thr Val Ser Ser
        115                 120                 125

```
<210> SEQ ID NO 12
<211> LENGTH: 127
<212> TYPE: PRT
<213> ORGANISM: Lama glama

<400> SEQUENCE: 12
```

Glu Val Gln Leu Gln Ala Ser Gly Gly Gly Leu Val Gln Ala Gly Asp
1               5                   10                  15

Ser Leu Arg Leu Ser Cys Ala Ala Ser Gly Arg Thr Ile Ser Thr
            20                  25                  30

Phe Ala Met Gly Trp Phe Arg Gln Ala Pro Gly Lys Glu Arg Glu Phe
        35                  40                  45

Val Ala Thr Ile Asn Trp Ser Gly Ser Ser Ala Arg Tyr Ala Asp Pro
 50                  55                  60

Val Lys Gly Arg Phe Thr Ile Ser Arg Asp Asp Ala Lys Asn Thr Val
 65                  70                  75                  80

Tyr Leu Glu Met Ser Ser Leu Lys Pro Glu Asp Ser Ala Val Tyr Tyr
                 85                  90                  95

Cys Ala Ser Gly Arg Tyr Leu Gly Gly Ile Thr Ser Tyr Ser Gln Gly
                100                 105                 110

Asp Phe Ala Pro Trp Gly Gln Gly Thr Gln Val Thr Val Ser Ser
                115                 120                 125

<210> SEQ ID NO 13
<211> LENGTH: 126
<212> TYPE: PRT
<213> ORGANISM: Lama glama

<400> SEQUENCE: 13

Glu Val Gln Leu Gln Ala Ser Gly Gly Gly Leu Val Gln Ala Gly Gly
 1               5                  10                  15

Pro Leu Arg Leu Ser Cys Ala Ala Ser Gly Arg Thr Asp Ser Thr Gln
                 20                  25                  30

His Met Ala Trp Phe Arg Gln Ala Pro Gly Lys Glu Arg Glu Phe Val
             35                  40                  45

Thr Ala Ile Gln Trp Arg Gly Gly Thr Ser Tyr Ala Asp Ser Val
 50                  55                  60

Lys Gly Arg Phe Thr Ile Ser Arg Asp Asn Ala Lys Asn Thr Val Tyr
 65                  70                  75                  80

Leu Glu Met Asn Ser Leu Glu Pro Glu Asp Thr Ala Val Tyr Tyr Cys
                 85                  90                  95

Ala Thr Asn Thr Arg Trp Thr Tyr Phe Ser Pro Thr Val Pro Asp Arg
                100                 105                 110

Tyr Asp Tyr Trp Gly Gln Gly Thr Gln Val Thr Val Ser Ser
            115                 120                 125

<210> SEQ ID NO 14
<211> LENGTH: 126
<212> TYPE: PRT
<213> ORGANISM: Lama glama

<400> SEQUENCE: 14

Glu Val Gln Leu Gln Ala Ser Gly Gly Gly Leu Val Gln Ala Gly Gly
 1               5                  10                  15

Pro Leu Arg Leu Ser Cys Ala Ala Ser Gly Arg Thr Asp Ser Thr Gln
                 20                  25                  30

His Met Ala Trp Phe Arg Gln Ala Pro Gly Lys Glu Arg Glu Phe Val
             35                  40                  45

Thr Ala Ile Gln Trp Arg Gly Gly Thr Ser Tyr Ala Asp Ser Val
 50                  55                  60

Lys Gly Arg Phe Thr Ile Ser Arg Asp Ser Ala Lys Asn Thr Val Tyr
 65                  70                  75                  80

Leu Glu Met Asn Ser Leu Lys Pro Glu Asp Thr Ala Val Tyr Tyr Cys
                 85                  90                  95

Ala Thr Asn Thr Arg Trp Thr Tyr Phe Ser Pro Thr Val Pro Asp Arg
                100                 105                 110

Tyr Asp Tyr Trp Gly Gln Gly Thr Gln Val Thr Val Ser Ser
            115                 120                 125

<210> SEQ ID NO 15
<211> LENGTH: 126
<212> TYPE: PRT
<213> ORGANISM: Lama glama

<400> SEQUENCE: 15

Glu Val Gln Leu Gln Ala Ser Gly Gly Gly Leu Met Gln Ala Gly Gly
1               5                   10                  15

Ser Leu Ser Leu Ser Cys Ala Ala Ser Gly Arg Thr Asp Ser Thr Gln
            20                  25                  30

His Met Ala Trp Phe Arg Gln Ala Pro Gly Lys Glu Arg Glu Phe Val
        35                  40                  45

Thr Ala Ile Gln Trp Arg Gly Gly Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Thr Asn Thr Arg Trp Thr Tyr Phe Ser Pro Thr Val Pro Asp Arg
            100                 105                 110

Tyr Asp Tyr Trp Gly Gln Gly Thr Gln Val Thr Val Ser Ser
        115                 120                 125

<210> SEQ ID NO 16
<211> LENGTH: 126
<212> TYPE: PRT
<213> ORGANISM: Lama glama

<400> SEQUENCE: 16

Glu Val Gln Leu Gln Ala Ser Gly Gly Gly Leu Val Gln Ala Gly Gly
1               5                   10                  15

Ser Leu Arg Leu Ser Cys Ala Ala Ser Gly Arg Thr Asp Ser Thr Gln
            20                  25                  30

His Met Ala Trp Phe Arg Gln Ala Pro Gly Lys Glu Arg Glu Phe Val
        35                  40                  45

Thr Ala Ile Gln Trp Arg Gly Gly Thr Ser Tyr Ala Asp Ser Val
    50                  55                  60

Lys Gly Arg Phe Thr Ile Ser Arg Asp Asn Ala Lys Asn Thr Val Tyr
65                  70                  75                  80

Leu Glu Met Asn Ser Leu Lys Pro Glu Asp Thr Ala Val Tyr Tyr Cys
                85                  90                  95

Ala Thr Asn Thr Arg Trp Thr Tyr Phe Ser Pro Thr Val Pro Asp Arg
            100                 105                 110

Tyr Asp Tyr Trp Gly Gln Gly Thr Gln Val Thr Val Ser Ser
        115                 120                 125

<210> SEQ ID NO 17
<211> LENGTH: 15
<212> TYPE: PRT
<213> ORGANISM: Artificial Sequence
<220> FEATURE:
<223> OTHER INFORMATION: synthetic construct

<400> SEQUENCE: 17

Gly Gly Gly Gly Ser Gly Gly Gly Gly Ser Gly Gly Gly Gly Ser
1               5                   10                  15